(12) United States Patent
Khanna et al.

(10) Patent No.: US 9,526,885 B1
(45) Date of Patent: Dec. 27, 2016

(54) MICRONEEDLES WITH SHARPENED TIPS AND CORRESPONDING METHOD OF FABRICATION

(71) Applicants: Puneet Khanna, Clifton Park, NY (US); Shekhar Bhansali, Tampa, FL (US)

(72) Inventors: Puneet Khanna, Clifton Park, NY (US); Shekhar Bhansali, Tampa, FL (US)

(73) Assignee: University of South Florida, Tampa, FL (US)

( * ) Notice: Subject to any disclaimer, the term of this patent is extended or adjusted under 35 U.S.C. 154(b) by 271 days.

(21) Appl. No.: 14/223,515

(22) Filed: Mar. 24, 2014

Related U.S. Application Data

(62) Division of application No. 12/845,221, filed on Jul. 28, 2010, now abandoned.

(60) Provisional application No. 61/229,571, filed on Jul. 29, 2009.

(51) Int. Cl.
*H01L 21/302* (2006.01)
*A61M 37/00* (2006.01)
*B44C 1/22* (2006.01)

(52) U.S. Cl.
CPC .......... *A61M 37/0015* (2013.01); *B44C 1/227* (2013.01); *A61M 2037/0053* (2013.01)

(58) Field of Classification Search
CPC .... B29C 33/38; B24B 19/16; A61M 37/0015; A61M 2037/0053; B44C 1/227
USPC ..... 216/2, 11, 12, 49, 79; 438/712, 713, 719
See application file for complete search history.

(56) References Cited

U.S. PATENT DOCUMENTS 6,406,638 B1 * 6/2002 Stoeber ................... B81B 1/006
216/11
7,901,387 B2 * 3/2011 Stemme ............ A61M 37/0015
604/173

OTHER PUBLICATIONS

Abhulimen, I. U., Characterization of Deep Reactive Ion Etching (DRIE) for via Formation in Chip Stacking Applications, University of Arkansas, UMI Microform No. 3317837, May 2008.

* cited by examiner

*Primary Examiner* — Duy Deo
*Assistant Examiner* — Maki Angadi
(74) *Attorney, Agent, or Firm* — Andriy Lytvyn; Smith & Hopen, P.A.

(57) ABSTRACT

Microneedles with sharpened tips are fabricated without any reduction to the shaft diameter below the tip. By sharpening the tip and not the entire length of the microneedle, their mechanical strength is maintained. The microneedles are fabricated out of a wafer substrate using lithography and deep reactive-ion etching (DRIE). By controlling the timing of the DRIE as the photoresist depletes, the sharpness and angle of the tips are controlled.

16 Claims, 4 Drawing Sheets

MICRONEEDLES WITH SHARPENED TIPS AND CORRESPONDING METHOD OF FABRICATION

CROSS-REFERENCE TO RELATED APPLICATIONS

This application is a divisional application of a pending U.S. Non-Provisional patent application Ser. No. 12/845,221 entitled "MICRONEEDLES WITH SHARPENED TIPS AND CORRESPONDING METHOD OF FABRICATION" filed on Jul. 28, 2010, which further claims priority to U.S. Provisional Patent Application No. 61/229,571 having the same title filed on Jul. 29, 2009.

STATEMENT OF GOVERNMENT INTEREST

This invention was made with Government support under Grant No. W81XWH-05-1-0585 awarded by the U.S. Department of the Army. The Government has certain rights in the invention.

BACKGROUND OF THE INVENTION

1. Field of the Invention

This invention relates to microneedles. More specifically, it relates to microneedles having sharpened sidewall tips and the corresponding method of fabricating them.

2. Description of the Prior Art

Many systems involve the transfer of physical entities through the skin, including needle puncture, electroporation, and removal of the stratum corneum through gels or tapes.

These methods, however, are all fairly intrusive. A minimally invasive method for sampling or delivering biological fluids is essential to autonomous therapy systems. Microneedles can achieve this task with significantly less trauma since their sharp tips and short lengths reduce the odds of encountering a nerve. They either do not penetrate deep enough to reach the underlying nerves, thus being totally painless, or they just graze the tips of nerves, causing sensation but reducing pain nevertheless.

An important design parameter in the fabrication of microneedles is the compromise between structural rigidity and ease of penetration. Due to the elasticity of skin, a considerable amount of deformation takes place around the insertion site, significantly reducing the insertion depth of microneedles. To mitigate the undesirable effects of skin deformation, the pressure applied by the needle tips needs to be increased. Insertion pressure can be increased by raising the applied force or by increasing the needle sharpness. An increase in applied force, however, intensifies the strain on the microneedles and may cause undue breakage. It may also magnify the patient's discomfort. Vibratory actuation has been suggested to decrease the force required for insertion. However, this requires the use of a vibratory actuator, which may not be possible for all applications, or might complicate the design requirements.

Permeation of microneedles can also be improved by increasing their sharpness. Sharpness is often achieved at the expense of structural rigidity. The needles must be capable of tolerating stresses related to the non-uniformity of the skin contour, inadvertent slippage during insertion or removal, and reasonable human movements during penetration. Microneedles with extremely sharp tips but thin needle bodies have been employed with successful penetration into the skin. However, structural damage after insertion was reported due to compromised sidewall thickness. Various approaches have used pyramidal or conical shaped structures to decrease the insertion area. Such designs achieve sharpening of the needle tip by gradually reducing the diameter of the lumen from the base to the tip. Reducing the lumen diameter, in general, reduces needle strength causing the top portions of the needles to be prone to breakage. Some other approaches have used a side-opened 'spearhead' structure at the tip of the needles. Apart from being extremely sharp, such designs also solve the issue of microneedle clogging; unfortunately, however, they also increase the fragility of the needles and are relatively complex to fabricate. Making the tip of the needles biodegradable is another approach having similar limitations. Yet another approach is fabricating needles with the entire length beveled. Such needles are relatively robust, however. Similarly, needles having only their tips beveled have been fabricated, but possess relatively limited sharpness.

Accordingly, what is needed in the art is a microneedle that easily penetrates the skin without increased applied force due to the microneedle's sharpness and rigidity. What is also needed is a method of fabricating said microneedle. However, in view of the prior art considered as a whole at the time the present invention was made, it was not obvious to those of ordinary skill in the art how the limitations of the art could be overcome.

SUMMARY OF THE INVENTION

The long-standing but heretofore unfulfilled need for an improved microneedle that easily penetrates the skin without increased applied force due to the microneedle's sharpness and rigidity is now met by a new, useful, and nonobvious invention.

Generally speaking, the present invention is a microneedle with a sharpened tip. The microneedle includes sidewalls that are sharpened only at the tip and not over the entire length of the microneedle. Sharpening only the tip ensures the mechanical stiffness of the microneedle is maintained. As a result, the required insertion force to penetrate the skin is reduced. This, in effect, increases the reliability of the microneedle.

Structurally, the microneedle includes a base having a fluid delivery channel formed within its backside. A needle extends from the front surface of the base and forms a passage through the base via the fluid delivery channel. The upper tip of the needle is tapered on both sides to create a sharpened tip. The sidewalls of the microneedle, however, are not sharpened below the tip. In this preferred embodiment, the microneedle is hollow; however, the term microneedle encompasses both hollow and solid microneedles. Accordingly, a solid microneedle would not include the passage through the base or the fluid delivery channel.

The method of fabricating the microneedle starts with a wafer substrate. Photoresist is applied to the back surface of the wafer substrate using lithography and outlines a fluid delivery channel. The fluid delivery channel is then etched into the backside of the wafer substrate using deep reactive-ion etching (DRIE). Photoresist is also applied to the front surface of the wafer substrate using lithography and outlines the sidewalls of the microneedle. The sidewalls of the microneedle are then etched into the front side of the wafer substrate using DRIE. The fluid delivery channel and needle form a passage through the wafer substrate.

The sharpening of the microneedle tip depends upon the controlled depletion of the photoresist and requires precise timing of the DRIE on the front side of the wafer substrate.

As the photoresist depletes on the front side of the wafer substrate during the DRIE, the gradual change in photoresist mask size creates a tapered etch profile at the tip of the microneedle sidewalls. The taper angle of the microneedles depends upon the etch rate of the wafer substrate as well as the depletion rate of the photoresist. Using this process, extremely sharp sidewall tips can be obtained, which greatly reduces the required skin penetration force. Also, such a design enables the use of larger lumen needles without a proportional increase in penetration force. This helps reduce blockage problems to which smaller lumen needles are often susceptible.

In addition, the aforementioned method to sharpen microneedles can be used to sharpen a variety of out-of-plane silicon structures other than microneedles.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
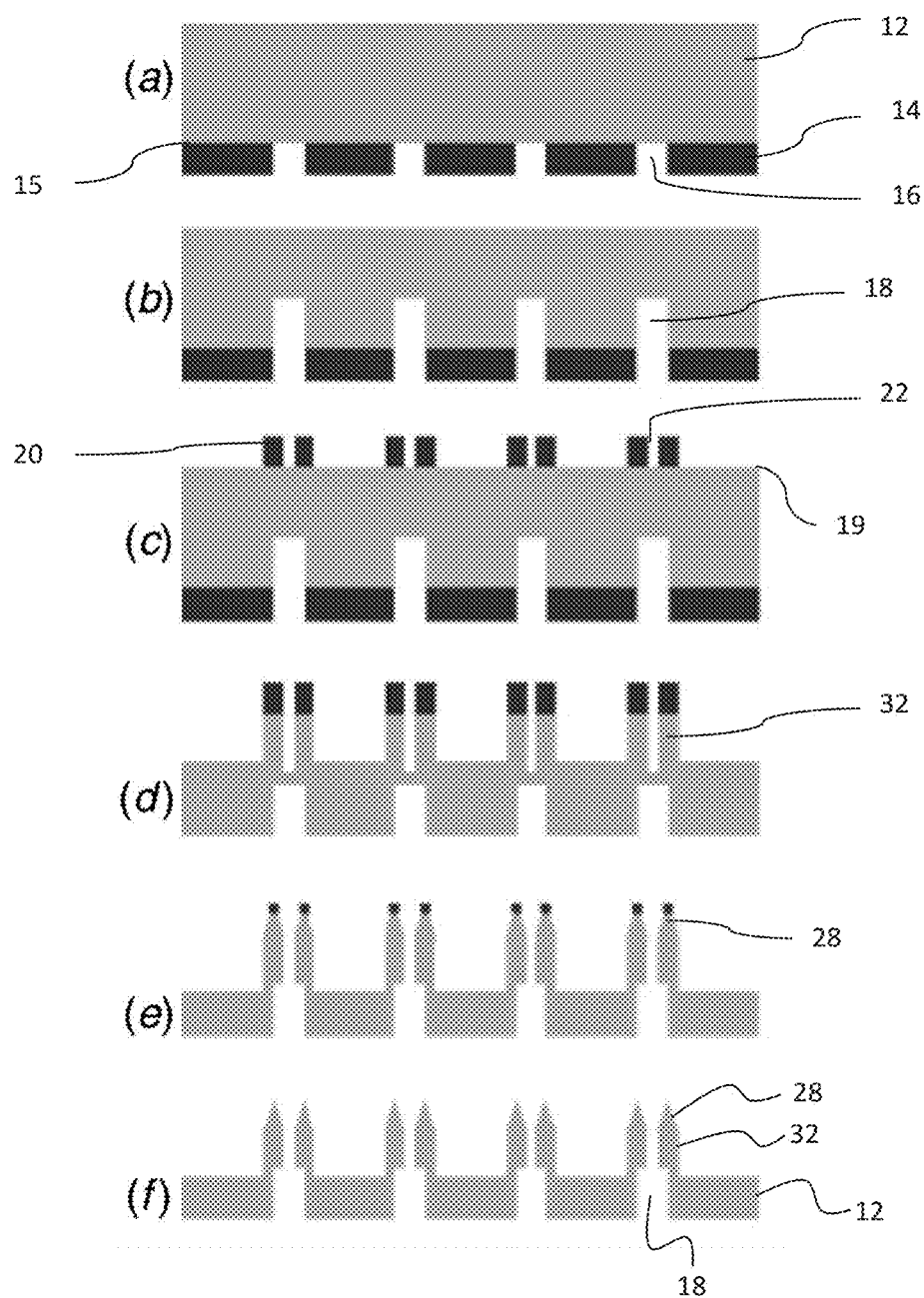
FIG. 1(a) is the first diagram of a six step animation depicting the novel fabrication process.
FIG. 1(b) depicts the second step of said six step animation.
FIG. 1(c) depicts the third step.
FIG. 1(d) depicts the fourth step.
FIG. 1(e) depicts the fifth step.
FIG. 1(f) depicts the sixth step.

Microneedles are fabricated out of a wafer substrate using lithography and deep reactive-ion etching (DRIE). As depicted in FIG. 1(a), lithography is performed on back surface 15 of wafer substrate 12. The lithography patterns photoresist 14 on back surface 15 of wafer substrate 12. Photoresist 14 forms circular holes 16 which outline channels 18 for fluid delivery. Next, as depicted in FIG. 1(b), fluid delivery channels 18 are etched into back surface 15 of wafer substrate 12 using DRIE. Lithography is then performed on front surface 19 of wafer substrate 12. As depicted in FIG. 1(c), the lithography patterns photoresist 20 on front surface 19 of wafer substrate 12. Photoresist 20 forms circular holes 22 which outline the microneedle sidewalls 32. Next, as depicted in FIG. 1(d), microneedles sidewalls 32 are etched on front surface 19 of wafer substrate 12 using DRIE.

Figure 2:
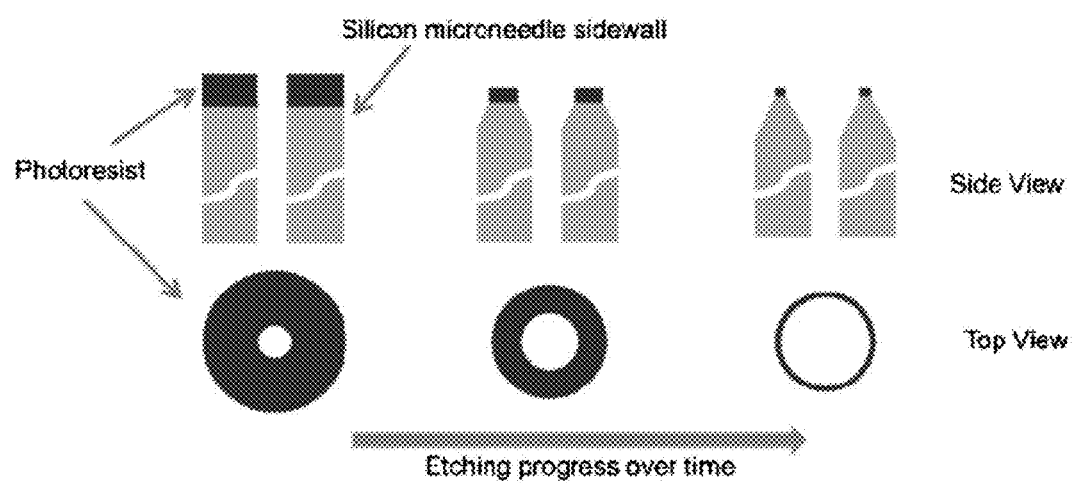
FIG. 2 is a diagram of the etching progress for sharpening the sidewall tip of a microneedle over time.

As depicted in FIG. 1(e), the sharpening of microneedle tips 28 depends upon the controlled depletion of the photoresist and requires precise timing of the DRIE performed on front surface 19 of wafer substrate 12. When most of the photoresist has been depleted, the resist loses its resolution and starts getting etched from the sides. The reduction of resist width corresponds to reduction of the annular ring area forming the protective mask. As illustrated in FIG. 2, the outer diameter of the annular resist ring reduces over time while the inner diameter increases over time. The gradual change in photoresist protective mask size during the DRIE causes a tapered etch profile to be created at the upper tip of the microneedle sidewalls.

To complete the process, a final solvent cleans the transformed wafer substrate and removes any residual photoresist, as depicted in FIG. 1(f).

The taper angle of the microneedles depends upon the etch rate of the wafer substrate as well as the depletion rate of the photoresist, i.e. the etch selectivity. By reducing the selectivity between the photoresist and the wafer substrate, a higher taper angle is obtained. A reduction in selectivity is brought about by appropriate changes in the DRIE recipe. In general, an increase in selectivity is brought about at the expense of a reduced etch rate. Maximum etch rate conditions are achieved when the residence time of reactive species is increased by using a lower total gas-flow rate or when the partial pressure of the reactive precursor gas is increased. The plasma-generated neutral chemical species do not readily etch the wafer substrate surface, but do play a role in the photoresist etching. By changing the interactive physical and chemical etching of the photoresist and the wafer substrate, the selectivity can be varied. This is usually implemented in plasma etch systems by independently controlling the power input to the plasma and the bias voltage applied to the wafer substrate.

Precise timing of the etch duration is critical. As soon as the entire resist is depleted, the microneedles are completely exposed to DRIE etching. Even a few minutes of over etching can result in complete loss of the needle tip. This is due to the inherent nature of the DRIE etching (Bosch process). During the first part of the Bosch process, polymer deposition takes place on the entire wafer substrate. The second part, the DRIE etch cycle, has a greater vertical component of etch rate than the horizontal component. Before the polymer on the vertical surfaces gets completely depleted during the etch cycle, the next polymer deposition cycle starts. The precise timing of cycles results in an almost total lack of lateral etching on vertical surfaces, such as the needle sidewalls. However, on a slanted surface, such as the needle tip, the polymer gets etched faster than it would on the sidewalls, due to an additional vertical etch component. Thus, the polymer on the slanted surface gets depleted completely before the next deposition cycle. Due to faster vertical than horizontal etching, as the process progresses, the slant increases and polymer depletion time reduces. In effect, the tip vanishes faster and faster, eventually leading to a flat 'blunt' top surface.

Parameters, such as tip angle, tip length, tip profile, the area inside the outer contour of the needle tip, and others, collectively define the relative level of tip sharpness. All of these parameters can be controlled as the photoresist depletes on the front side of the wafer substrate during the DRIE by controlling the length of the DRIE and the etch selectivity.

In an exemplary embodiment, the needles are fabricated out of a 4 inch, 400 µm thick, (100) oriented, double side polished silicon wafer substrate. Lithography is performed on the backside of the wafer using photoresist AZ P4620. The lithography patterns the wafer with circular holes outlining the through-wafer microfluidic channels for fluid delivery. DRIE (Alcatel AMS 100 SDE) is performed on the backside of the wafer, forming approximately 200 m deep holes. (The DRIE recipe is: Etch step—SF6 at 300 sccm with 3 sec. cycle; Passivation step—C4F8 at 200 sccm and O2 at 20 sccm with 1.4 sec. cycle; Pressure—$5.25 \times 10^{-1}$ mTorr; Source generator power—2400 W; Substrate holder power—Used in pulsed mode, High cycle at 100 W for 25 millisecond, Low cycle at 0 W for 75 millisecond; Substrate holder He pressure—$9.75 \times 10^{-3}$ mTorr; Bias Voltage—negative 185 V.) Lithography is then performed on the front side of the wafer, again using photoresist AZ P4620. This step outlines the microneedle sidewalls. Next, DRIE of the silicon wafer is done using a similar etch recipe as stated above to form the microneedles sidewalls. The microneedles ranged from 33 gauge (i.e., outer and inner diameters of 200 μm and 100 μm, respectively) to 36 gauge (i.e, outer and inner diameters of 100 m and 30 μm, respectively).

Figure 3:
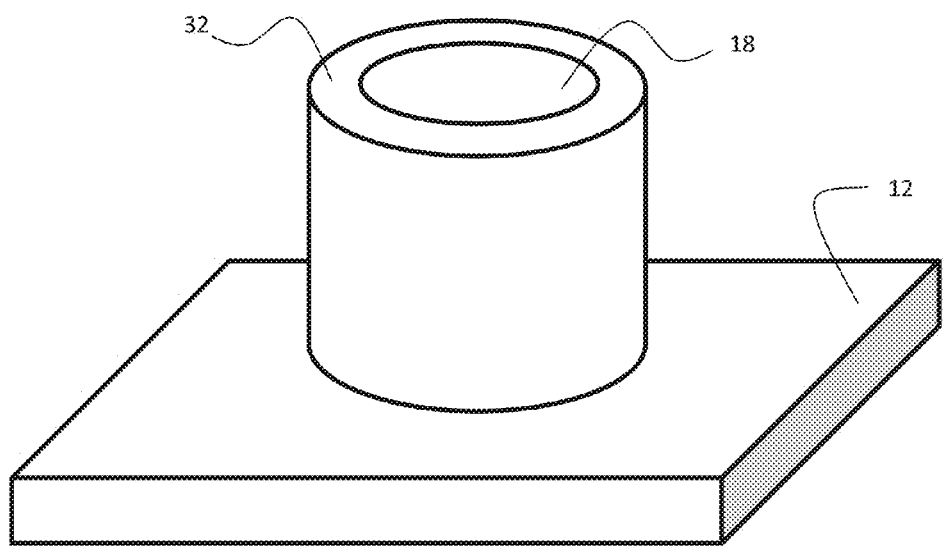
FIG. 3 is an upper perspective view of an unsharpened microneedle.
Figure 4:
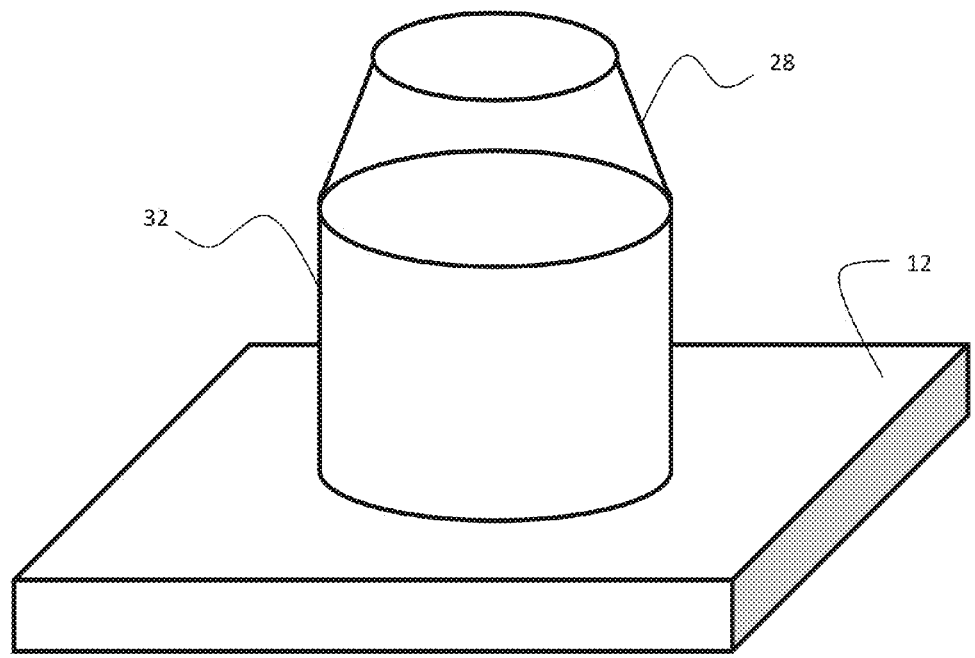
FIG. 4 is an upper perspective view of a sharpened microneedle.

FIG. 3 depicts a microneedle having an unsharpened tip. In contrast, FIG. 4 depicts a microneedle having a sharpened tip.

Figure 5:
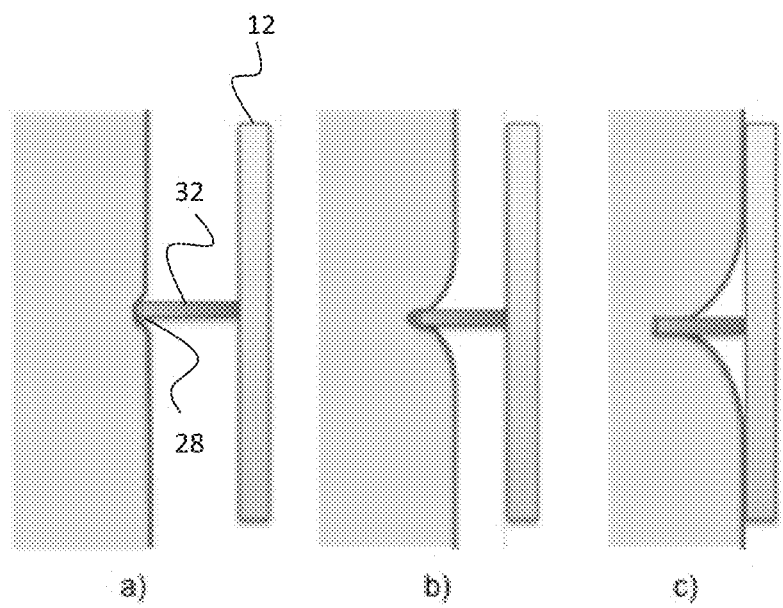
FIG. 5(a) is the first diagram of a three step animation depicting a microneedle being inserted into the skin.
FIG. 5(b) is the second animation of said three step animation.
FIG. 5(c) is the third step of said animation.

The proposed insertion technique of the microneedles into skin is depicted in FIGS. 5(*a*)-(*c*). Initially, the microneedle forms a slight indentation on the top surface of skin, as shown in FIG. 5(*a*). As the microneedle moves further into the skin, the skin deformation increases, as shown in FIG. 5(*b*). The skin gets deformed before rupturing due to inherent resistance to penetration. The amount of resistance ability of skin can be thought of as a potential energy stored within it. When the energy incident via the needles surpasses the potential energy within the skin, penetration occurs. At this point, the penetration is relatively instantaneous, especially at high insertion forces. FIG. 5(*c*) depicts a post-insertion of the microneedle. At the instant of penetration, the skin moves slightly towards the needle array, thus registering a force drop. After insertion, the base of the array touches the skin surface and continues to push forward. As sharper needles are used, the needles puncture the skin faster, and after relatively lesser deformation.

In a preferred embodiment, the microneedle is hollow. A hollow microneedle allows for the administration of fluids. However, the term microneedle encompasses both hollow and solid microneedles. Accordingly, a solid microneedle would not include the passage through the base or the fluid delivery channel.

The aforementioned method of sharpening microneedles can be used to sharpen a variety of out-of-plane silicon structures other than microneedles (e.g., to create a wedge or straight knife edge). Photoresist may be applied to a substrate in a variety of patterns using lithography and the substrate etched as desired using DRIE. Any number of structures may be formed by controlling the length of the DRIE and the etch selectivity.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method for fabricating a microneedle having a sharpened sidewall tip, comprising the steps of:
    providing a wafer substrate;
    applying a first layer of photoresist to a backside of the wafer substrate using lithography, the first layer of photoresist on the backside of the wafer substrate having a pattern outlining a channel for fluid delivery;
    etching a fluid delivery channel into the backside of the wafer substrate using deer reactive-ion etching (DRIE);
    applying a second layer of photoresist to a front side of the wafer substrate using lithography, the second layer of photoresist on the front side of the wafer substrate having a pattern outlining a needle for fluid delivery;
    etching an extruding needle into the front side of the wafer substrate using DRIE, the fluid delivery channel and the extruding needle forming a passage there through; and
    sharpening an upper tip of the extruding needle by using DRIE to deplete the second layer of photoresist and etch sidewalls of the extruding needle, whereby as the second layer of photoresist depletes on the front side of the wafer substrate, a tapered etch profile at the upper tip of the extruding needle is created.

2. A method for fabricating a microneedle having a sharpened sidewall tip as in claim 1, further comprising the step of:
    controlling the taper angle of the upper tip of the extruding needle by varying etch selectivity.

3. A method for fabricating a microneedle having a sharpened sidewall tip as in claim 1, further comprising the step of:
    applying a solvent to remove any residual photoresist.

4. A method for fabricating a microneedle having a sharpened sidewall tip as in claim 1, further comprising the step of:
    forming the wafer substrate of silicon.

5. A method for fabricating a microneedle having a sharpened sidewall tip as in claim 1, further comprising the step of:
    forming the photoresist on the backside of the wafer substrate in an annular pattern outlining a channel for fluid delivery.

6. A method for fabricating a microneedle having a sharpened sidewall tip as in claim 1, further comprising the step of:
    forming the fluid delivery channel within the backside of the wafer substrate in an annular configuration.

7. A method for fabricating a microneedle having a sharpened sidewall tip as in claim 1, further comprising the step of:
    forming the photoresist on the front side of the wafer substrate in an annular pattern outlining a needle for fluid delivery.

8. A method for fabricating a microneedle having a sharpened sidewall tip as in claim 1, further comprising the step of:
    forming the extruding needle on the front side of the wafer substrate in an annular configuration.

9. A method for fabricating a microneedle having a sharpened sidewall tip, comprising the steps of:
    providing a wafer substrate;

applying a first photoresist layer to a backside of the wafer substrate using lithography, the first photoresist layer having a pattern outlining a channel for fluid delivery;

etching a fluid delivery channel into the backside of the wafer substrate using deep reactive-ion etching (DRIE);

applying a second photoresist layer to a front side of the wafer substrate using lithography, the second photoresist layer having a pattern outlining a needle for fluid delivery;

etching the second photoresist layer using DRIE to create a microneedle on the front side of the wafer substrate, the fluid delivery channel being disposed within the microneedle; and gradually depleting the second photoresist layer to create a tapered etch profile at the upper tip of the microneedle using DRIE.

10. A method for fabricating a microneedle having a sharpened sidewall tip as in claim 1, further comprising the step of:

controlling the taper angle of the upper tip of the microneedle by varying etch selectivity.

11. A method for fabricating a microneedle having a sharpened sidewall tip as in claim 1, further comprising the step of:

applying a solvent to remove any residual photoresist.

12. A method for fabricating a microneedle having a sharpened sidewall tip as in claim 1, further comprising the step of:

forming the wafer substrate of silicon.

13. A method for fabricating a microneedle having a sharpened sidewall tip as in claim 1, further comprising the step of:

forming the photoresist on the backside of the wafer substrate in an annular pattern outlining a channel for fluid delivery.

14. A method for fabricating a microneedle having a sharpened sidewall tip as in claim 1, further comprising the step of:

forming the fluid delivery channel within the backside of the wafer substrate in an annular configuration.

15. A method for fabricating a microneedle having a sharpened sidewall tip as in claim 1, further comprising the step of:

forming the photoresist on the front side of the wafer substrate in an annular pattern outlining a needle for fluid delivery.

16. A method for fabricating a microneedle having a sharpened sidewall tip as in claim 1, further comprising the step of:

forming the extruding needle on the front side of the wafer substrate in an annular configuration.

\* \* \* \* \*